United States Patent [19]

Howse

[11] 4,364,880
[45] Dec. 21, 1982

[54] METHOD FOR MAKING A BREAST PROSTHESIS

[76] Inventor: Jeanette W. Howse, Rte. 3 Box 908, St. Cloud, Fla. 32769

[21] Appl. No.: 228,709

[22] Filed: Jan. 16, 1981

[51] Int. Cl.³ .......................... B29C 5/08; B29C 9/08
[52] U.S. Cl. ........................................... 264/28; 3/36; 264/213; 264/245; 264/255; 264/275; 264/279; 264/294; 264/299; 264/338
[58] Field of Search .................. 264/28, 130, 222, 250, 264/294, 347, 336, DIG. 60, DIG. 30, 213, 259, 271.1, 275, 299, 245, 255; 3/36; 2/267; 128/463, 478-481

[56] References Cited

U.S. PATENT DOCUMENTS

| | | | |
|---|---|---|---|
| 2,580,264 | 12/1951 | Wright et al. | 264/DIG. 30 |
| 2,651,783 | 9/1953 | Wright et al. | 2/267 |
| 3,811,133 | 5/1974 | Harris | 3/36 |
| 4,019,209 | 4/1977 | Spence | 264/DIG. 30 |
| 4,086,666 | 5/1978 | Vaskys | 264/222 |
| 4,184,214 | 1/1980 | Shaper et al. | 128/463 |
| 4,199,825 | 4/1980 | Knoche | 3/36 |
| 4,317,241 | 3/1982 | Knoche | 264/222 |

Primary Examiner—Willard E. Hoag
Attorney, Agent, or Firm—Duckworth, Allen, Dyer & Pettis

[57] ABSTRACT

Method for making a breast prosthesis formed from plasticized polyvinylchloride plastic having coloring, texture, weight and feel closely approximating those of a natural breast. Liquid plastic is heated and tinted with a first portion having a skin tone and a second portion having the darker color of the areola and nipple area. The darker portion is poured into a breast mold to the depth of the desired areola area. This pour is allowed to set until tacky at which time the skin colored portion is poured, which bonds to the first pour. The mold is immediately cooled in a freezer at 5° F. or less. After curing and cooling, the prosthesis is removed from the mold. An alternative embodiment used for teaching self-examination includes small objects embedded in the prosthesis to simulate tumors.

8 Claims, 8 Drawing Figures

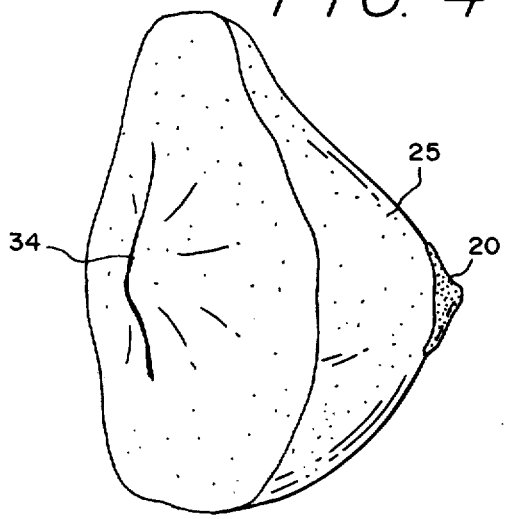
FIG. 4
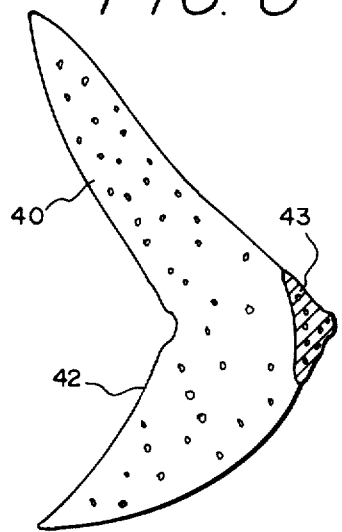
FIG. 6
FIG. 5
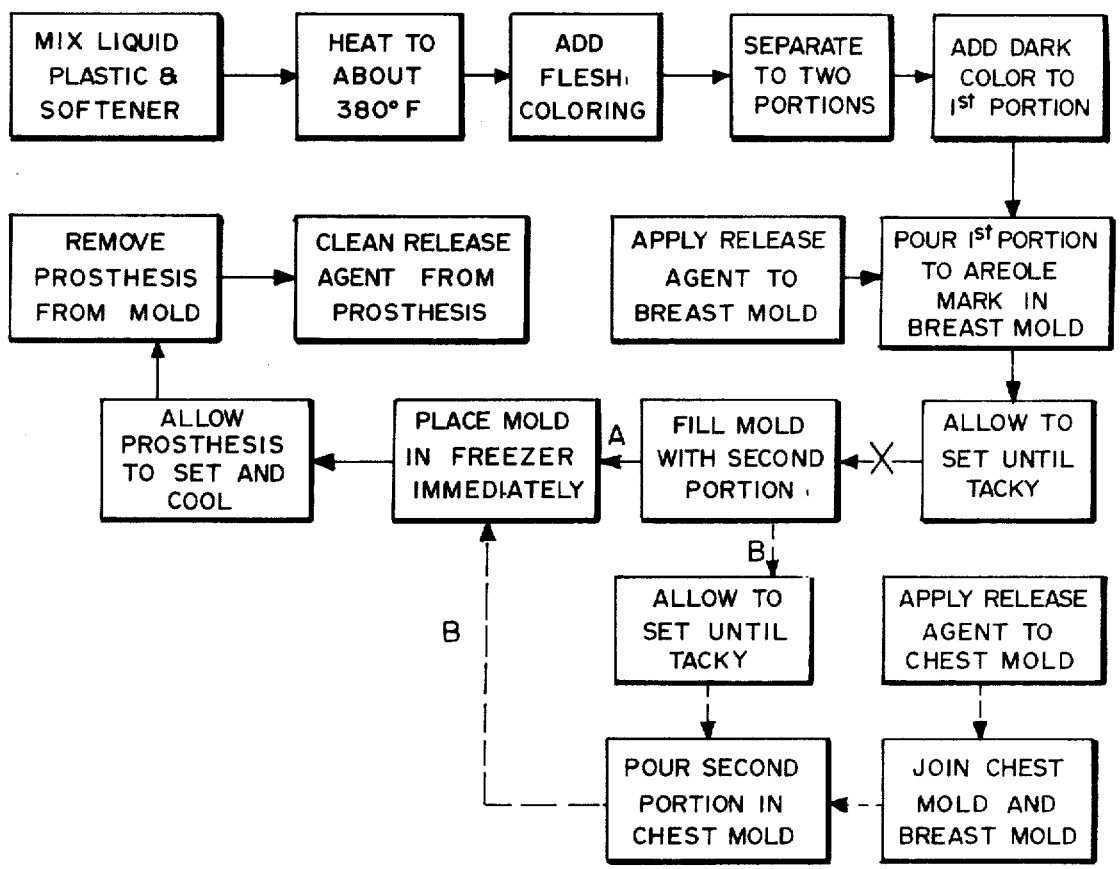

METHOD FOR MAKING A BREAST PROSTHESIS

BACKGROUND OF THE INVENTION

1. Field of the Invention

The present invention relates to a breast prosthesis and to a method of forming the prosthesis.

2. Description of the Prior Art

A very large number of women in the United States have had and will have surgical removal of the breast and the underlying muscular tissue. While such surgery is effective in curing the original malignancy, it often introduces severe psychological problems. In many cases, the person becomes very self-conscious of her appearance and can develop feelings of loss of femininity and the like.

These problems can, in many instances, be overcome or greatly reduced by a breast prosthesis which will be comfortable to wear, that can be used with almost any type of clothing without detection, and which will install confidence in the wearer. In addition to the obvious cosmetic use of a breast prosthesis, it should satisfy several other basic requirements. Its weight should correspond to that of the remaining breast and be distributed so that the upper body is balanced so as to feel natural to the user while walking or engaging in any physical activity.

The material from which the breast prosthesis is formed should approximate the characteristics of the natural breast in several areas. For example, it should be compressible under application of pressure and have a "feel" similar to that of the natural breast. In addition, its movement when the woman moves, walks, or runs should be in a generally vertical direction as occurs with the natural breast.

There have been a number of artificial breasts produced from various types of materials, many of which have attempted to meet some of the above requirements. One type, molded from a resilient plastic material, is described in U.S. Pat. No. 4,184,214 to Schaper, et al. and utilizes a hollow cavity in the form of a cup spring to achieve some of these desired characteristics. Others have been formed from laminated foam rubber as exemplified by U.S. Pat. No. 2,814,808 to Burman. A patent to Harris, U.S. Pat. No. 3,811,133 discloses a hollow plastic form filled with resilient wadding and a discrete weight to attempt to match the resiliency and weight of the natural breast. Spence has disclosed, in U.S. Pat. No. 4,019,209, an artificial breast formed from a gel material and covered with a porous elastic fabric cover. However, none of these or other known breast prosthesis meet fully all of the above listed requirements. Therefore, there is a great need for a method of producing a breast prosthesis which is as close as possible to the natural breast so as to contribute to an improved mental attitude, good personal feeling, and natural appearance of the user.

SUMMARY OF THE INVENTION

I have developed a novel breast prosthesis and method of forming the prosthesis which, in accordance with my invention, will provide all of the above delineated features. The invention provides a method of producing a custom breast prosthesis which accurately fits the wearer and gives her the same appearance she had before the removal of the natural breast. The basis of my prosthesis is a special plastic material which, when processed in accordance with my method, closely matches the color, feel, and weight of the human breast.

As will be described in more detail hereinafter, the plastic is formed from two liquids which are poured into a mold in two or three stages. Special coloring material is available for the plastic and is added during processing to achieve the desired coloring to match that of the patient.

A first portion of the liquid plastic is colored to match the darker nipple and areola tone of the patient and is poured first into the mold to a predetermined depth to produce the nipple and areola area of the prosthesis. After a predetermined time, a second portion of the plastic colored to match the patient's normal skin tone is poured in a manner which bonds the second portion to the first poured portion. The second pour develops the major mass of the prosthesis. In some patients having deeply scarred areas or cavities, a mold thereof is used to make a third pour for a matching rear portion of the prosthesis which is then combined with the breast portion first poured.

The plastic is maintained at about 380° F. during the pouring. I have found that a sudden cooling or chilling of the molded prosthesis immediately after completion of the pouring to a temperature less than 10° F. advantageously produces a surface closely approximately the texture and feel of natural skin. Thus, I quickly cool the prosthesis in the mold before removing until it is reduced to approximately room temperature.

Upon removing the breast prosthesis from the mold, it is ready for cleaning and use.

I have found that the resulting product is similar in weight and texture to normal breast tissue and can be worn with no discomfort. Due to the texture of the plastic, a firm contact with the chest area occurs preventing the prosthesis from slipping or moving around under clothing. Therefore, the wearer can engage in normal activities, even of a very active nature, without embarrassment due to movement of the prosthesis. No special pockets in the brassiere or special brassiere is needed. When felt through the clothing, there is no discernible difference in feel to that of the natural breast. Due to the natural coloring of the flesh portion and the nipple and areola, the prosthesis of my invention can be worn under a sheer and lace brassiere and will appear very natural. The plastic is impervious to water and can therefore be used in swimming. It is not damaged by skin lotions or the like and may be easily cleansed with mild liquid soaps. The prosthesis will retain its shape and texture over a long period of time.

It is therefore a principal object of the invention to provide a breast prosthesis and method for forming same which will have the appearance, weight, texture, and other characteristics of the natural breast.

It is another object of the invention to provide a method of producing a custom breast prosthesis which will closely match a patient's remaining breast in size, shape, weight and appearance.

It is still another object of the invention to produce a breast prosthesis which is durable and long lasting.

It is yet another object of the invention to provide a breast prosthesis which will not absorb water or lotions and that can be easily and quickly cleaned and dried.

It is a further object of the invention to provide a breast prosthesis which may be custom formed to fit scars or depressions in the chest of the wearer and which has a chest contacting surface which prevents the prosthesis from moving or slipping underneath the clothing.

It is still a further object of the invention to provide a breast prosthesis which can be worn with almost any type of clothing including sheer apparel and which will be difficult to detect and which can be worn by a very active person without danger of embarrassment.

These and other objects and advantages of the invention will become apparent from the following detailed description and the drawings.

BRIEF DESCRIPTION OF THE DRAWINGS

FIG. 4 is a three dimensional view of the breast prosthesis from the mold of FIG. 3 showing a rear surface for matching the chest depression;

FIG. 5 is a simplified flow diagram showing the operation of forming breast prosthesis by the method of the invention;

FIG. 6 is a cross sectional view of an artificial breast produced by the method of the invention for use over a small natural breast to enhance the appearance thereof;

DETAILED DESCRIPTION OF THE PREFERRED EMBODIMENT

My invention is a female breast prosthesis formed from a resilient plastic and the novel method of making the prosthesis. An important element of the invention is the nature of the plastic used for forming of the breast prosthesis as well as certain critical steps in the making thereof. The preferred material is a polyvinylchloride (PVC) in a form which is resilient when cured. As is known in the art, the addition of stabilizers and plasticizers to the PVC stock will produce this form of the plastic. Although the plastic in form for molding and curing is available from many sources, I prefer to use a type available from MF Manufacturing, Inc., Post Office Box 18442, Fort Worth, Tex. This source furnishes a liquid plastic under stock number 228LP and a liquid softener stock number 4116S. This source also have available compatible liquid coloring material under stock number 3309. As will be described in more detail hereinafter, I generally utilize MF white, MF red, MF brown, and MF yellow coloring.

Referring to FIGS. 1 through 3 and FIG. 5, the steps in forming the breast prosthesis of the invention will be described. It is necessary to have a mold which preferably is a close match to the patient's remaining breast. It is common to utilize plaster of paris molds and several known techniques may be used to produce the mold. For example, a female mold of the remaining breast of a patient may be formed by application of strips of moistened plaster of paris bandage to the breast to obtain a perfect impression when hardened. After the plaster of paris strips are hardened and removed, the inside of the initial mold may be coated with quick drying latex rubber. After setting, the rubber may be removed, turned inside out to thereby form a casing or shape having the same contour as the natural breast but for the opposite side. As may be now recognized, this casing can be used to form a male plaster model, and a female plaster mold made from the first plaster model. More detail on this technique may be found in U.S. Pat. No. 2,580,264 to M. A. Wright, et al. Other methods of obtaining molds which will provide a match to the remaining breast will be known to those of skill in the art.

Figure 1:
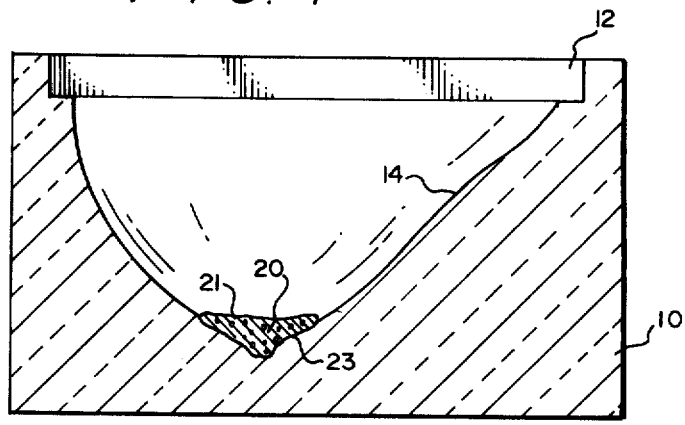
FIG. 1 shows a cross section of a typical mold for molding the breast prosthesis of the invention showing a pour of the nipple and areola portion.
Figure 2:
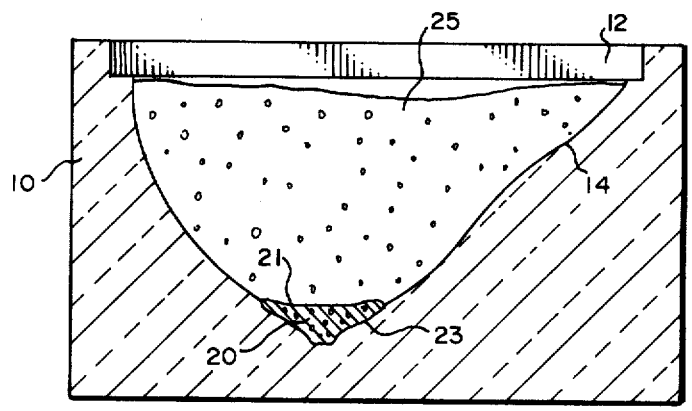
FIG. 2 is a cross section of the mold of FIG. 1 having the remainder of the breast prosthesis poured.
Figure 3:
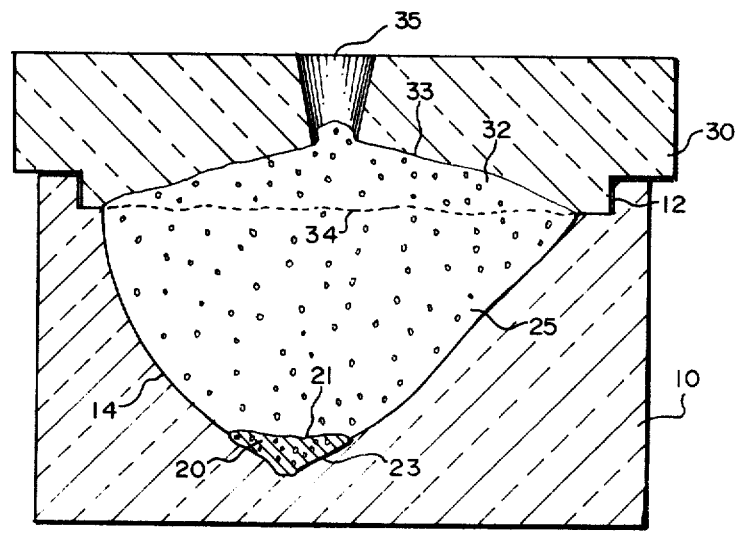
FIG. 3 is a cross sectional view of the mold of FIG. 1 fitted with a second mold for producing a rear surface of the breast prosthesis to fit a chest area having depressions therein.

In FIGS. 1 through 3, a female mold 10 is shown in cross section formed from plaster of paris or the like and which will be utilized in the method of the invention. Mold 10 comprises three parts. The inner contour 14 of the breast; contour 23 of the nipple and areola portion, and inset 12 for mating with a second mold 30 as shown in FIG. 3. The type of mold 30 is not necessary in all prosthesis but is advantageous for a patient who may have deep scars or depressions in the chest area and is utilized to provide a mating portion of the prosthesis to fit such chest depressions. Thus, mold 30 may be formed with a contour 33 to match the chest of the patient.

The first step in forming a breast prosthesis in accordance with the invention is to prepare the plastic material for use. For purposes of illustration, certain specific quantities will be indicated. However, it may be understood that the quantities will be varied in accordance with the size of the prosthesis. The liquid plastic is mixed with plastic softener in a heating pot in the ratio of one and one half pints of plastic to one pint of plastic softener. The mixture is stirred gently and heated to approximately 380° F. Although plasticized polyvinylchloride is normally heated in the range of 320° to 325° F., I have found it necessary to increase this temperature to 380° F. to achieve the natural external appearance and feel of the breast prosthesis. During the mixing of the softener and the plastic, care must be taken to prevent creation of air bubbles. Mixing is sufficient when the material becomes clear. At this point, the mixture is maintained at approximately 380° F. for about one minute.

The next step is to color the mixture to a desired flesh color. A typical flesh color may be obtained for a plastic mixture of two and one half pints by adding the following: one ounce of MF white coloring; one drop of MF red plastic coloring; two drops MF brown plastic coloring; and two drops MF yellow plastic coloring. Since it is very desirable to obtain a close match to the patient's skin color, a selection of sample blocks of plastic may be made in which the amounts of the coloring agents are varied from block to block and a number assigned to each block so that the ratios of color to plastic is known for each sample. With a set of such color blocks running from an extremely light skin tone to a deeply tanned skin tone, a match may be determined during an examination of the patient and prior to the making of that patient's prosthesis.

After addition of the coloring, the temperature is maintained and the material stirred to evenly distribute the color. At this point, the skin tone colored plastic mixture is separated into two portions. The first portion requires about one-quarter cup of the mixture. While maintaining this first portion at the approximately 380° F. temperature, a portion of a drop of the MF red color and of the MF brown color is added to produce a darker color tint for the nipple and areola area of the prosthesis. As in the flesh tone colors, color samples may be made up over a range of tones for matching to the patient. With the first and second portions maintained at about 380° F., pouring of the prosthesis may proceed. Before pouring, a release agent must be applied to the surfaces 14 and 23 of the mold 10. Although many effective release agents are available, I have found that a high quality of vegetable oil, such as Wesson oil, is effective. After coating the inner surface of mold 10 with the oil, it is blotted to remove excess surface oil. Mold 10 is marked to show the outer perimeter of the areola area by a light scratch in the plaster of paris as indicated at 21. The first portion is poured into surface 23 of mold 10 until it reaches the marked line 21. I have found that, in most cases, this pour requires about one to one and one half tablespoons, of the liquid plastic. The nipple and areola pour is allowed to cool for about twenty seconds until the surface is just becoming tacky. At that point, the second portion having the flesh tint which has been maintained at 380° F. is poured very slowly into mold surface 14 on top of the poured nipple-areola portion. This pour is done with care to permit the hotter flesh tinted portion to meld into the nipple pour so as to form a continuous surface. I have found that circling the outside nipple area by pouring to the sides of the lower portion of the mold and then covering the first pour with about one half inch plastic before continuing to pour the mold to the desired amount provides the desired molding. If the first pour is allowed to cool too long until it starts to set, the second pour will not adhere. Therefore, care must be taken in this step of my method.

Referring to FIG. 1, it may be noted that the nipple-areola area has been poured as indicated at 20 to line 21. In FIG. 2, the second portion of the liquid plastic having the flesh tone has been poured at 25 to form the remainder of the breast prosthesis. The shape as shown is suitable for a patient in which the chest area is not deeply scarred. However, if the patient has scars or depressed areas in the chest, it is advisable to utilize the second mold 30 shown in FIG. 3. In this case, portion 25 is filled to the top of the mold as indicated by dash line 34. Mold 30 which has a funnel-like opening 35 in the top portion thereof is made ready. Just as the surface 34 becomes slightly tacky as previously discussed with respect to nipple and areola portion 20, mold 30 is fitted in inset portion 12 and the chest portion 32 is poured via opening 35 until filled. The 380° F. liquid plastic will melt into surface 34 of portion 25 to form an integral prosthesis. The small overpour portion in opening 35 may later be trimmed off.

Referring to the poured prosthesis in either FIG. 2 or FIG. 3, immediately after completion of the pour the entire mold is placed in a freezer unit having a temperature in the range of 0° to 10° F. I have determined that the rapid cooling of the hot plastic in combination with the oil release agent in the mold causes a very natural skin surface appearance to the finished breast prosthesis. For a medium size prosthesis, approximately one to one and one half hours is required in the freezer unit. Larger sizes may require up to three hours.

After the mold is thoroughly cooled, the prosthesis can be removed from the mold. The sides of the prosthesis are slowly separated from the mold by a slightly circular motion and the finished prosthesis is lifted carefully from the mold. The form is then submerged in cool water, removed and blotted dry to remove the excess oil therefrom.

A breast prosthesis molded using the method of my invention will have a weight and texture of the breast tissue which closely matches that of the patient's natural breast. The prosthesis is normally worn in a standard well fitting brassiere; however, no special brassiere or pocketed type cup is needed. The surface and resilience of the material forming the back of the prosthesis tends to cause the form to slightly adhere to the chest area and therefore will not move or slip underneath the clothing. In the case of the prosthesis molded as shown in FIG. 3, and as shown in three dimensional view in FIG. 4, the custom molded portion 34 will fit deep scarring or depressed portions of the wearer's chest and is thus secured from moving or slipping while being worn.

If care is taken in the flesh tone coloring as well as the nipple coloring, the prosthesis may be worn under sheer garments and will appear very natural.

The prosthesis made in accordance with my invention is very durable and does not absorb water. Therefore, it may be used while in swimming and may be easily cleaned with any mild soap. Advantageously, the form can be washed, rinsed, and dried with a towel very quickly when required.

Referring now to FIG. 5, the major steps in practicing my method of forming the novel breast prosthesis described above may be noted. This flow chart indicates by following the flow arrows through arrow A, the method of molding the prosthesis illustrated in FIG. 2 while following alternative arrows B, the prosthesis shown in FIG. 3 and FIG. 4 will result.

While I have described my invention showing certain specific embodiments, I understand that various modifications will be obvious from these teachings to those of skill in the art. My invention is therefore not to be restricted except as necessary with respect to prior art. While I have also shown a method for production of breast prosthesis for use by persons having had mastectomies, my method is equally applicable to the manufacturer of custom artificial breasts which may be used by persons having small breasts to provide better fit of clothing and to enhance their appearance and to produce instructional artificial breasts for training women in self-examination.

Turning to FIG. 6, a cross sectional view of an artificial breast of this type is shown. A mold of the type shown in FIGS. 1 and 2 may be used with a second mold portion of the type of mold 30 shown in FIG. 3 but with a plug portion molded from the natural breast of the wearer. This plug would have the shape 42 of the artificial breast 40 of FIG. 6 which would produce an artificial breast 40 that would exactly fit the user thereby being more comfortable and natural appearing than prior art artificial breasts. Since it is common for a woman to have slightly unsymmetrical breasts, separate molds would be made for left and right breasts so as to ensure a satisfactory fit of the two artificial breasts. As may be noted, surface 42 of the artificial breast 40 of FIG. 6 includes a nipple recess which serves to prevent irritation to the wearer as may occur with prior art artificial breasts. In forming custom artificial breasts 40, the nipple and areola area 43 may be formed to suit the user's requirements.

The method described in detail above for making breast prostheses and artificial breasts which have a lifelike texture, feel and appearance is also admirably suited for a training aid to assist women in learning to make self-examination for early detection of growths in the breast which may be malignant. Although written material, motion pictures, and personal instruction are all available to train women to examine their breasts for detection of lumps at an early stage, there has been no reliable way to demonstrate how such lumps actually feel. Therefore, I have adapted by invention to provide doctors and clinics with instructional artificial breasts having various types and sizes of lumps molded therein which may then be used in training women in self-examination techniques and having the ability to illustrate the feel of lumps.

Figure 7:
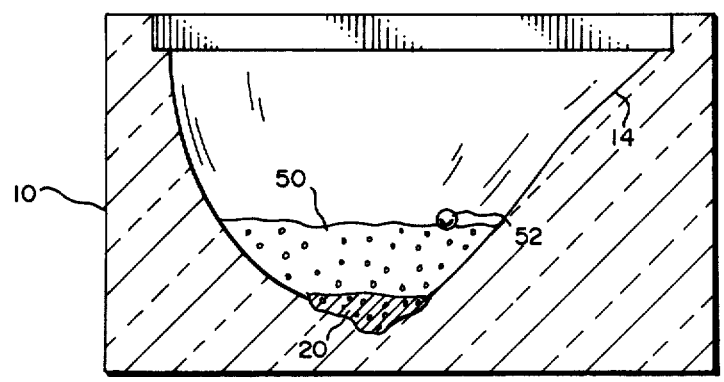
FIG. 7 is a cross sectional view of a breast mold showing the introduction of an object to represent a lump in the artificial breast.
Figure 8:
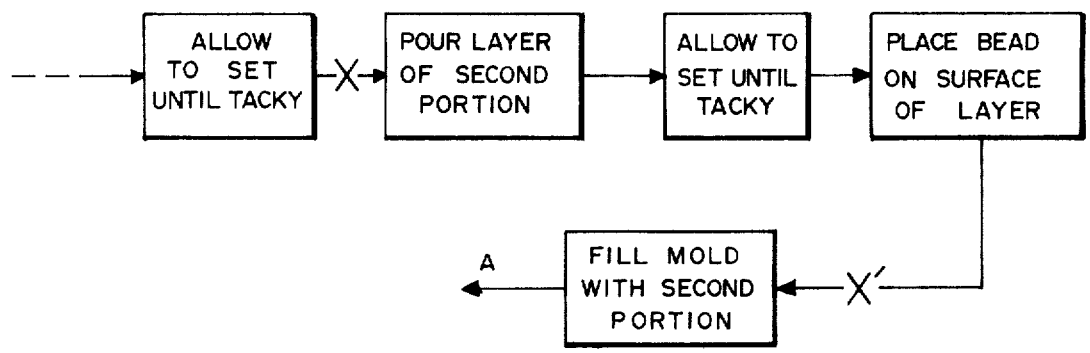
FIG. 8 is a simplified flow diagram showing the additional steps between flow points X and X' for the diagram of FIG. 5 to produce an instructional artificial breast.

Turning now to FIGS. 7 and 8, details of this alternative embodiment of my invention is shown. In FIG. 7, a typical mold 10 for a breast as previously discussed is shown. The work flow diagram of FIG. 8 between the flow arrows marked X and X' illustrates the additional steps required for this implementation of my invention. With the illustrated steps X to X' of FIG. 8 substituted for the line X in FIG. 5, that figure describes my novel method for producing my instructional artificial breast. The nipple and areola part 20 is poured as previously described with reference to FIG. 5 and a small part of the second portion is poured as indicated at 50. After the portion 20 has set until tacky, a part of the second portion of the heated liquid plastic is poured to produce layer 50 as shown in FIG. 7. Layer 50 is allowed to set until tacky and a small object 52, such as a wood bead, is pushed into the tacky surface to represent a lump. After this step, the mold is filled level with the top and cured as described above with reference to FIG. 5. The additional steps in FIG. 5 indicated by the dashed flow arrows B are not used in this implementation. After curing, the instructional artificial breast is removed from mold 10 and is preferably mounted on a flat baseboard by cementing or the like.

In using the instructional aid, the instructor can demonstrate to the student how to feel around the periphery of the breast form with the fingers and, thereafter, require the student to indicate when she has found the lump produced by object 52. I contemplate that the doctor or clinic would utilize a plurality of my instructional aids having different sizes and shapes of lumps distributed in various portions of the artificial breast. For example, there are in general two types of lumps that may be found. One type may be relatively hard and immovable, while other types may be somewhat soft and may be shifted within the tissue. Some lumps may be roughly spherical while others may be striated or elongated. To demonstrate these various types, lump models may be formed from both hard and soft plastic as well as being formed into these various shapes and sizes. Thus, very realistic simulation of typical lumps both benign and malignant, may be used in accordance with my invention. However, in the teaching process, the student would not normally be instructed to differentiate between malignant and benign forms since such diagnosis must be left to the doctor.

As previously discussed, the PVC plastic forming the instructional artificial breast can be easily cleaned after use. Due to its realistic appearance and natural texture and feel, the device is very effective as a training aid to teach women to locate suspicious lumps in their breasts at an early date permitting prompt diagnose and treatment if necessary.

I claim:

1. A method of forming a female breast prosthesis using a mold comprising the steps of:
   heating an uncured liquid plasticized or polyvinylchloride plastic to a temperature greater than the curing temperature of the plastic;
   tinting a first portion of the heated liquid plastic to a selected first color representative of the color of the nipple and areola of a human female breast;
   tinting a second portion of the heated liquid plastic to a selected second color representative of the color of a human female skin;
   coating the mold with a release agent;
   pouring the first portion of the heated liquid plastic into the nipple-areola portion of the mold;
   partially curing the poured liquid plastic until it becomes slightly tacky;
   pouring the second portion of the heated liquid plastic into the mold and over the nipple-areola portion to a preselected level in the mold to form the breast prosthesis;
   chilling the mold immediately after pouring the second portion to a selected low temperature much lower than ambient; and
   curing the breast prosthesis in the mold at the selected low temperature.

2. A method of forming a custom female breast prosthesis for a patient having a depressed chest region using a first mold of the breast, nipple and areola, and a second mold of the depressed chest region comprising the steps of:
   heating an uncured liquid plasticized polyvinylchloride plastic to a temperature greater than the curing temperature of the plastic;
   tinting a first portion of the heated liquid plastic to a selected first color representative of the color of the nipple and areola of a human female breast;
   tinting a second portion of the heated liquid plastic to a selected second color representative of the color of a human female skin;
   coating the mold with a release agent;
   pouring the first portion of the heated liquid plastic into the nipple-areola portion of the mold;
   partially curing the poured liquid plastic until it becomes slightly tacky;
   pouring a first part of the second portion of the heated liquid plastic into the mold and over the nipple-areola portion to a preselected level in the mold to form the breast prosthesis;
   joining the second mold to the first mold;
   partially curing the second-poured liquid plastic until it becomes slightly tacky;
   pouring a second part of the second portion of the heated liquid plastic into the second mold and over the slightly tacky second-poured partially cured plastic;
   chilling the molds, immediately after pouring the second part of the second portion, to a selected low temperature much lower than ambient; and
   curing the breast prosthesis in the mold at the selected low temperature.

3. The method as defined in claim 1 or 2 in which the release agent is a vegetable oil.

4. The method as defined in claim 1 or 2 in which the step of heating an uncured liquid plasticized polyvinylchloride plastic includes the steps of:
   mixing and uncured liquid plasticized polyvinylchloride plastic with a liquid softening agent in the ratio of one and one half-to-one to produce a mixture; and holding the mixture at approximately 380° F. for approximately one minute.

5. The method as defined in claim 1 or 2 in which the steps of chilling the mold and curing the breast prosthesis includes the steps of:

exposing the mold to a temperature in the range of about 0° to 10° F.; and maintaining such temperature for a period of about one and one quarter to three hours.

6. The method as defined in claim 1 or 2 in which the uncured liquid plastic is heated to about 380° F.

7. The method as defined in claim 6 in which the mold is chilled to a temperature in the range of about 0° to 10° F.

8. A method of forming an instructional artificial breast using a mold and comprising the steps of:

heating an uncured liquid plasticized polyvinylchloride plastic to a temperature greater than the curing temperature of the plastic;

tinting a first portion of the heated liquid plastic to a selected first color representative of the color of the nipple and areola of a human female breast;

tinting a second portion of the heated liquid plastic to a selected second color representative of the color of a human female skin;

coating the mold with a release agent;

pouring the first portion of the heated liquid plastic into the nipple-areola portion of the mold;

partially curing the poured liquid plastic until it becomes slightly tacky;

pouring a part of the second portion of the heated liquid plastic into the mold and over the nipple-areola portion to a preselected level in the mold;

partially curing the poured second portion of the liquid plastic until it becomes slightly tacky;

placing an object representative in size and shape of a breast tumor on the surface of the tacky layer;

pouring an additional part of the second portion of the heated liquid plastic into the mold over the tacky layer and object to fill the mold therewith;

chilling the mold immediately after completion of pouring to a selected low temperature much lower than ambient; and curing the breast prosthesis in the mold at the selected low temperature.

* * * * *